United States Patent [19]

Wu et al.

[11] Patent Number: 5,877,369
[45] Date of Patent: Mar. 2, 1999

[54] HYDROCARBON CONVERSION CATALYST COMPOSITION AND PROCESSES THEREFOR AND THEREWITH

[75] Inventors: An-hsiang Wu, Bartlesville; Charles A. Drake, Nowata, both of Okla.

[73] Assignee: Phillips Petroleum Company, Bartlesville, Okla.

[21] Appl. No.: 955,908

[22] Filed: Oct. 23, 1997

[51] Int. Cl.$^6$ .............................. C07C 2/52; C07C 5/333; B01J 23/00
[52] U.S. Cl. .......................... 585/419; 585/407; 585/418; 585/654; 585/660; 585/661; 502/84; 502/325; 502/339; 502/352; 502/353; 502/354
[58] Field of Search .............................. 502/84, 325, 339, 502/349, 352, 353, 354; 585/407, 418, 419, 654, 660, 661

[56] References Cited

U.S. PATENT DOCUMENTS

| | | | |
|---|---|---|---|
| 3,625,867 | 12/1971 | Yoshino et al. | 502/349 |
| 3,887,495 | 6/1975 | Juguin et al. | 502/311 |
| 3,890,246 | 6/1975 | Grasselli et al. | 502/202 |
| 3,994,832 | 11/1976 | Antos | 502/334 |
| 4,221,738 | 9/1980 | Imai | 502/325 |
| 4,389,337 | 6/1983 | Eastman | 252/462 |
| 4,409,133 | 10/1983 | Tremont et al. | 502/354 |
| 4,431,750 | 2/1984 | McGinnis et al. | 502/329 |
| 4,716,143 | 12/1987 | Imai | 502/326 |
| 5,073,662 | 12/1991 | Obrich | 585/660 |
| 5,665,223 | 9/1997 | Bogdan | 502/349 |

Primary Examiner—Elizabeth D. Wood
Attorney, Agent, or Firm—Lucas K. Shay

[57] ABSTRACT

A catalyst composition and a process for using of the catalyst composition in a hydrocarbon conversion process are disclosed. The composition comprises an inorganic support, a Group VA metal or metal oxide, and optionally a Group IVA metal or metal oxide and a Group VIII metal or metal oxide. The process comprises contacting a fluid which comprises at least one saturated hydrocarbon with the catalyst composition under a condition sufficient to effect the conversion of the hydrocarbon to an olefin. Also disclosed is a process for producing the catalyst composition.

53 Claims, No Drawings

HYDROCARBON CONVERSION CATALYST COMPOSITION AND PROCESSES THEREFOR AND THEREWITH

FIELD OF THE INVENTION

This invention relates to a catalyst composition useful for converting a saturated hydrocarbon to an olefin, a process for producing the composition, and a process for using the composition in a hydrocarbon conversion process.

BACKGROUND OF THE INVENTION

It is well known to those skilled in the art that olefins are a class of very important industrial chemicals which find a variety of uses in petrochemical industry such as, for example, in production of various organic compounds and polymers. Olefins can be produced by several different methods such as, for example, thermal cracking of saturated hydrocarbons and catalytic dehydrogenation of saturated hydrocarbons.

It is conventional in the dehydrogenation of saturated hydrocarbons to utilize catalysts such as platinum, nickel-kieselguhr, chromium oxide-alumina, zinc oxide-alumina, and platinum-alumina. Additionally, a platinum catalyst on a support, with or without oxygen present, is known to be one possible system for the dehydrogenation of paraffin hydrocarbons in the presence of steam.

A process for the dehydrogenation of alkanes, cycloalkanes and arylalkanes can also be carried out over a catalyst composition comprising a Group VIII metal, such as platinum, or a mixture of a Group VIII metal and a Group IVA metal, such as tin. Such catalyst is generally deposited on a support selected from the group consisting of alumina, HF-treated alumina, silica, zinc oxide, magnesia, zirconia, aluminum silicate, and Group IIA and Group IIB aluminate spinels. A dehydrogenation process can be materially improved when the process is conducted in the presence of gaseous hydrogen or mixtures of gaseous hydrogen and gaseous oxygen.

However, in the known processes, the conversion of a saturated hydrocarbon to an olefin and the selectivity thereto are generally not as high as one skilled in the art would desire. Accordingly, there is an ever-increasing need to develop a catalyst and a process for converting a saturated hydrocarbon to the more valuable olefins (hereinafter referred to as hydrocarbon conversion process). Such development would also be a significant contribution to the art and to the economy.

SUMMARY OF THE INVENTION

An object of this invention is to provide a catalyst composition which can be used to convert a saturated hydrocarbon to an olefin. Also an object of this invention is to provide a process for producing the catalyst composition. Another object of this invention is to provide a process which can employ the catalyst composition to convert a saturated hydrocarbon to olefins. An advantage of the catalyst composition is that it exhibits high hydrocarbon conversion activity, satisfactory yield of olefins, and good selectivity. Other objects and advantages will becomes more apparent as this invention is more fully disclosed hereinbelow.

According to a first embodiment of the present invention, a composition which can be used as catalyst for converting a saturated hydrocarbon or a mixture of hydrocarbons containing at least one saturated hydrocarbon to an olefin or a mixture of olefins is provided. The composition comprises at least one metal or metal oxide selected from Group VA metals, an inorganic support, optionally at least one metal or metal oxide selected from Group IVA metals, and further optionally at least one metal or metal oxide selected from Group VIII metals. The terms "Group IVA", "Group VA", and "Group VIII" refer to the Periodic Table of the Elements, CRC Handbook of Chemistry and Physics, 67th edition, 1986–1987, CRC Press, Boca Raton, Fla.

According to a second embodiment of the invention, a process for producing a composition which can be used as catalyst in a hydrocarbon conversion process is provided. The process can comprise, consist essentially of, or consist of the steps: (1) combining a Group VA metal compound, an inorganic support, and optionally a Group IVA metal compound and/or a Group VIII metal compound to from a mixture, and (2) calcining the mixture under a condition sufficient to convert each metal compound to its oxide form.

According to a third embodiment of the present invention, a process which can be used for converting a saturated hydrocarbon or mixture of hydrocarbons containing at least one saturated hydrocarbon to an olefin or a mixture of olefins is provided which comprises, consists essentially of, or consists of, contacting a fluid which comprises a saturated hydrocarbon or mixture of hydrocarbons, optionally in the presence of an inert fluid, with a catalyst composition which can be the same as disclosed above in the first embodiment of the invention under a condition effective to convert a saturated hydrocarbon to an olefin or a mixture of olefins.

DETAILED DESCRIPTION OF THE INVENTION

According to the first embodiment of the invention, a composition which can be used as catalyst in a hydrocarbon conversion process for converting a saturated hydrocarbon to an olefin is provided. As used herein, the term "hydrocarbon" is generally referred to, unless otherwise indicated, as one or more hydrocarbons, saturated or unsaturated, having 1 to about 30 carbon atoms, preferably 2 to about 20 carbon atoms, more preferably 2 to about 16, and most preferably 2 to 10 carbon atoms per molecule. Also preferably, the hydrocarbon is an aliphatic saturated hydrocarbon, a mixture of saturated aliphatic hydrocarbons, or a mixture of saturated aliphatic hydrocarbons and unsaturated hydrocarbons. An example of hydrocarbons include, but are not limited to, ethane, propanes, butanes, pentanes, heptanes, octanes, nonanes, dodecanes, gasoline, or combinations of two or more thereof. The composition can comprise, consist essentially of, or consist of, an inorganic support having incorporated therein, or impregnated thereon, a selectivity-improving amount of a promoter to improve the yield of or selectivity to an olefin when the composition is used in a hydrocarbon conversion process. The term "improving" or "improve" is referred to, unless otherwise indicated, as an increased weight percent of, or percent selectivity to, olefin in the product stream of a hydrocarbon conversion process using a promoted catalyst such as $Bi_2O_3$-promoted silica, as compared to using a nonpromoted catalyst.

The term "metal" used herein refers to, unless otherwise indicated, both "metal" and "element" of the Periodic Table of the Elements because some elements in the Periodic Table of the Elements may not be considered as metals by those skilled in the art.

According to the first embodiment of the invention, the weight percent of the Group IVA, Group VA, or Group VIII metal or element in the composition of the invention can be any weight % so long as the weight % can improve the yield of or selectivity to an olefin in a hydrocarbon conversion process for converting of a hydrocarbon to a an olefin. Generally, the weight % of Group IVA or Group VIII metal can be in the range of from about 0.0001 to about 5%, preferably about 0.005 to about 3%, more preferably about 0.05 to about 2%, and most preferably from 0.1 to 1.5% for an effective hydrocarbon conversion. generally, the weight % of Group VA metal in the composition of the invention can be in the range of from about 0.1 to about 50%, preferably about 0.5 to about 40%, more preferably about 1 to about 30%, and most preferably 1 to 20%.

Any metal that, when incorporated into an inorganic material such as silica, is capable of improving a hydrocarbon conversion process to an olefin can be employed in the invention. Presently, it is preferred that the promoter comprises at least one Group VA metal, optionally at least one Group VIII metal, and further optionally at least one Group IVA metal. The preferred Group VA metal is bismuth or oxide thereof. The preferred Group VIII metal is platinum or an oxide thereof. The preferred Group IVA metal is tin or an oxide thereof. The oxidation state of the metal can be any available oxidation state. For example, in the case of a platinum or a platinum oxide, the oxidation state of platinum can be 0 (metal only), 2, 4, or combinations of two or more thereof. If a combination of metals or metal oxides is employed, the molar ratio of the second metal or metal oxide, or the third metal or metal oxide, or the fourth metal or metal oxide to the first metal or metal oxide can be in the range of about 0.01:1 to about 100:1.

Any commercially available inorganic support known to one skilled in the art which can catalyze the conversion of a hydrocarbon to an olefin can be employed in the present invention. Examples of suitable inorganic support include, but are not limited to, inorganic oxides, spinels, or combinations of two or more thereof. The inorganic oxide can be a clay, an alumina, a silica, or combinations of two or more thereof. If a spinel support is used, the metal of the spinel is selected from the group consisting of zinc, magnesium, iron, manganese, calcium, zirconium, molybdenum, ruthenium, rhenium, cobalt, germanium, and combinations of two or more thereof. The presently preferred inorganic oxide is an alumina or silica. The presently preferred spinel is zinc aluminate, calcium aluminate, zinc titanate, magnesium aluminate, or combinations of two or more thereof. These spinels are readily available and effective. The inorganic support, when present, generally makes up the rest of the composition.

In a preferred embodiment, the composition of the invention is a physical combination of composition A and composition B in which composition A comprises, consists essentially of, or consists of at least one Group IVA metal, at least one Group VIII metal, and an inorganic support disclosed above. Also preferably, composition A comprises, consists essentially of, or consists of at least one Group IVA metal support on a first inorganic support and at least one Group VIII metal supported on a second inorganic support which can be the same as the first inorganic support which can be one or more inorganic oxides or spinels disclosed above. Example of composition A is a platinum/tin-promoted zinc aluminate/calcium aluminate which is disclosed in the U.S. Pat. No. 5,073,662, disclosure of which is incorporated herein by reference.

Composition B of the composition of the invention can comprise, consist essentially of, or consist of at least one Group VA metal and an inorganic support. An example of composition B is a bismuth-promoted silica.

Composition A and composition B can be physically combined using any means known to one skilled in the art such as blending and extrusion. The weight ratio of composition A to composition B can be any ratio so long as the ratio can produce the weight % of each component disclosed above. Generally the ratio can be in the range of from about 0.1:1 to 10:1.

According to the present invention, an inorganic support and the metal promoters can be well mixed at about 15° to about 100° C. under atmospheric pressure, generally in a liquid such as water or a hydrocarbon, by any means known to one skilled in the art such as stirring, blending, kneading, or extrusion, following which the resulting mixture can be dried in air at a temperature in the range of from about 20° to about 800° C., for about 0.5 to about 50 hours under any pressures that accommodate the temperatures, preferably under atmospheric pressure. Thereafter, the dried, mixture can be further heat-treated at a temperature in the range of from about 200° to 1000° C., preferably about 250° to about 750° C., and most preferably 350° to 650° C. for about 1 to about 30 hours to prepare the present composition. However, it is preferred that the composition be produced by the process disclosed in the second embodiment of the invention.

In the second embodiment of the invention, an inorganic support can be combined with a Group IVA compound, and a Group VIII compound, preferably in a solution or suspension, under a condition well known to those skilled in the art to incorporate a compound into an inorganic support. Because the methods for incorporating or impregnating a compound into an inorganic support such as, for example, impregnation by incipient wetness method, are well known to those skilled in the art, the description of which is also omitted herein for the interest of brevity.

According to the second embodiment of the invention, a preferred process for producing the composition of the invention comprises, consists essentially of, or consists of the steps: (1) contacting an inorganic support with a Group IVA compound under a condition sufficient to incorporate the Group IVA compound into the inorganic support to form a first composition; (2) heat-treating the first composition under a condition to effect the production of a heat-treated first composition; (3) incorporated a Group VIII compound into the heat-treated first composition to produce a second composition; and (4) calcining or steaming the second composition to produce composition A. The incorporation of Group VIII compound in step (3) can be carried out with a second inorganic oxide to produce a second composition, which after heating, can be physically combined with the first composition.

Generally, in the first step of the process of the preferred process of the second embodiment of the invention, at least one inorganic support can be combined with at least one Group IVA compound in any suitable weight ratios which would result in the weight % of a Group IVA metal or metal oxide disclosed in the first embodiment of the invention. Presently it is preferred that such combination be carried out in a suitable liquid, preferably an aqueous medium, to form an incipient wetness inorganic support-metal compound mixture. The combining of an inorganic support and a Group IVA compound can be carried out at any temperature. Generally, the temperature can be in the range of from about 15° C. to about 100° C., preferably about 20° C. to about 100° C., and most preferably 20° C. to 60° C. under any pressure, preferably atmospheric pressure, for any length so long as the metal compound and the zeolite are well mixed, generally about 1 minute to about 15 hours, preferably about 1 minute to about 5 hours.

Another preferred process for producing the composition of the invention comprises, consists essentially of, or consists of: (1) contacting an inorganic support with a Group IVA compound and a Group VIII compound under a condition sufficient to incorporate the Group IVA compound and the Group VIII compound into the inorganic support to form a first composition; (2) heat-treating the first composition under a condition to produce composition A. The incorporation of Groups IVA and VIII compounds into an inorganic support can be the same as the incorporation of Group IVA compound disclosed above.

Any Group IVA compounds can be used in the first step of the preferred process of the second embodiment. Examples of suitable tin compound include, but are not limited to, tri-n-butyltin acetate, n-butyltin trichloride, di-n-butyldiphenyltin, di-n-butyltin diacetate, di-n-butyltin dichloride, di-t-butyltin dichloride, di-n-butyltin dilaurate, dimethyldiphenyltin, diphenyltin dichloride, hexa-n-butylditin, hexamethylditin, hexaphenylditin, methyltin trichloride, phenyltin trichloride, tetra-n-butyltin, tetraethyltin, tetramethyltin, tetraphenyltin, tetra-i-propyltin, tetra-n-propyltin, tin acetate, tin bromide, tin chloride, tin oxalate, tin sulfate, tin sulfide, and combinations of any two or more thereof. The presently preferred tin compound is a tin chloride such as $SnCl_2 \cdot 2H_2O$.

Examples of suitable germanium-containing compounds include, but are not limited to, germanium chloride, germanium bromide, germanium ethoxide, germanium fluoride, germanium iodide, germanium methoxide, and combinations of any two or more thereof.

Upon completion of incorporating a Group IVA compound into an inorganic support, a first composition is formed. In the next step of the process, the first composition is subject to a heat treatment. The heat treatment can be air calcining or steam. Air calcining can be carried out under a condition sufficient to convert a metal compound to its oxide form and can include a temperature in the range of from about 300° C. to about 1000° C., preferably about 350° C. to about 750° C., and most preferably 400° C. to 650° C. under a pressure in the range of from about 1 to about 10, preferably about 1 atmospheres for a period in the range of from about 1 to about 30, preferably about 1 to about 20, and most preferably 1 to 15 hours.

Steam treatment can be carried out under a suitable condition sufficient to effect the conversion of a Group IVA compound, which have been incorporated into the first composition, to its corresponding oxide form. The first composition can be air dried to remove most moisture content before being steam-treated. Air drying can be carried out at a temperature for about 25° C. to about 150° C. for about 1 minute to about 30 hours under any effective pressure that can maintain the necessary temperature. The air-dried first composition can then be treated with a steam. Generally the steam temperature can be in any suitable vessel and in the range of from about 120° C. to about 1500° C., preferably about 200° C. to about 1200° C., and most preferably 250° C. to 1000° C. The treatment period can be as short as 5 minutes to as long as about 30 hours so long as it is sufficient to convert the metal compound to its oxide form. The treatment can be carried out under a pressure which can maintain the required temperature and can be in the range of from about atmospheric pressure to about 2,000, preferably to about 1,500, and most preferably to 1000 psig.

Upon completion of heat treatment, a heat-treated first composition is produced which can then be contacted, generally mixed, with a Group VIII compound. The contacting of the first composition with a Group VIII compound can be carried out under a condition that is sufficient to effect the incorporation of the Group VIII compound into the first composition. Generally the condition can be the same as that disclosed above for contacting a first inorganic support with a Group IVA compound. In this step, a second composition is produced. The second composition can then be subject to a heat treatment as described to produce composition A of this invention.

Any Group VIII compound can be used in the present invention. The presently preferred Group VIII compound is a platinum compound. Generally, any platinum compound that can promote the combining of platinum element with a zeolite can be employed herein. Examples of suitable platinum compounds include, but are not limited to, chloroplatinic acid ($H_2PtCl_6 \cdot xH_2O$), platinum chloride (platinic chloride), platinum bromide, platinum iodine, tetramine platinum chloride ($Pt(NH_3)_4Cl_2 \cdot H_2O$ or $Pt(NH_3)_4Cl_2$), tetramine platinum nitrate ($Pt(NH_3)_4(NO_3)_2$), tetramine platinum hydroxide ($Pt(NH_3)_4(OH)_2$), tetrachlorodiamine platinum, and combinations of any two or more thereof. The oxidation state of platinum in the above-illustrated platinum compound can be any available oxidation state. The presently preferred platinum compound is chloroplatinic acid for it is readily available.

Examples of other suitable Group VIII compounds include, but are not limited to, cobalt acetate, cobalt acetylacetonate, cobalt acetylacetonate, cobalt benzoylacetonate, cobalt bromide, cobalt carbonate, cobalt chloride, cobalt 2-ethylhexanoate, cobalt fluoride, cobalt iodide, cobalt 2,3-naphthalocyanine, cobalt nitrate, cobalt oxalate, cobalt perchlorate, cobalt phthalocyanine, cobalt sulfate, cobalt thiocyanate, cobalt tungstate, nickel acetate, nickel acetylacetonate, nickel bromide, nickel carbonate, nickel chloride, nickel nitrate, nickel perchlorate, nickel phosphide, nickel sulfate, nickel sulfide, nickel titanate, palladium acetate, palladium acetylacetonate, palladium bromide, palladium iodide, palladium nitrate, palladium sulfate, palladium sulfide, rhodium acetate, rhodium acetylacetonate, rhodium bromide, rhodium chloride, rhodium nitrate, rhodium octanoate, rhodium phosphate, rhodium sulfate, rhenium nitrate, rhenium sulfate, and combinations of any two or more thereof.

Composition B can be produced by the same process disclosed above for the production of the heat-treated first composition except that a Group VA compound is used. It can also be produced by mixing a Group VA compound and an inorganic support by, for example, extrusion followed by heat treatment as disclosed above.

Any Group VA compound can be used. The presently preferred Group VA compounds are bismuth compounds. Examples of suitable bismuth compounds include, but are not limited to, bismuth acetate, bismuth bromide, bismuth chloride, bismuth 2-ethylhexanoate, bismuth fluoride, bismuth iodide, bismuth neodecanoate, bismuth nitrate, bismuth oxide, bismuth sulfide, bismuth titanate, triphenylbismuth, and combinations of two or more thereof.

The invention composition can then be produced by physical combination such as, for example, blending, extrusion, of composition A and composition B under any suitable condition known to one skilled in the art such as, for example, blending at room temperature under atmospheric pressure for about 1 minute to about 20 hours.

The composition of the invention then can be, if desired, pretreated with a reducing agent before being used in a hydrocarbon conversion process. The presently preferred reducing agent is a hydrogen-containing fluid which comprises molecular hydrogen (H$_2$) in the range of from 1 to about 100, preferably about 5 to about 100, and most preferably 10 to 100 volume %. The reduction can be carried out at a temperature, in the range of from about 250° C. to about 800° C. for about 0.1 to about 10 hours preferably about 300° C. to about 700° C. for about 0.5 to about 7 hours, and most preferably 350° C. to 650° C. for 1 to 5 hours.

According to the third embodiment of the present invention, a process useful for converting a hydrocarbon to an olefin comprises, consists essentially of, or consists of contacting a fluid stream comprising a saturated hydrocarbon or a mixture of saturated hydrocarbons and, optionally, in the presence of an inert fluid with a catalyst composition under a condition sufficient to effect the conversion of a saturated hydrocarbon to an olefin. The inert fluid can be hydrogen, nitrogen, helium, argon, carbon dioxide, neon, steam, and combinations of any two or more thereof. The presently preferred inert fluid is steam. The inert fluid can also be fed separately into contact with a hydrocarbon and a catalyst. The catalyst composition can be the same as that disclosed in the first embodiment of the invention. The term "fluid" is used herein to denote gas, liquid, vapor, or combinations of two or more thereof.

Any fluid which contains a saturated hydrocarbon as disclosed above can be used as the feed for the process of this invention. Generally, the fluid feed stream can also contain olefins, naphthenes (cycloalkanes), or some aromatic compounds.

The contacting of a fluid feed stream containing a saturated hydrocarbon with the catalyst composition can be carried out in any technically suitable manner, in a batch or semicontinuous or continuous process, under a condition effective to convert an aliphatic hydrocarbon to an olefin. Generally, a fluid stream as disclosed above, preferably being in the vaporized state, is introduced into a suitable reactor having a fixed catalyst bed, or a moving catalyst bed, or a fluidized catalyst bed, or combinations of two or more thereof by any means known to one skilled in the art such as, for example, pressure, meter pump, and other similar means. Because a hydrocarbon conversion reactor is well known to one skilled in the art, the description of which is omitted herein for the interest of brevity. The condition can include a weight hourly space velocity (WHSV) of the fluid stream in the range of about 0.01 to about 100, preferably about 0.05 to about 50, and most preferably 0.1 to 30 g feed/g catalyst/hour. The inert fluid hourly space velocity can be in the range of from about 0.01 to about 5000 ft$^3$/ft$^3$ catalyst/hour. Generally, the pressure can be in the range of from about 0 to about 1000 psig, preferably about 0 to about 200 psig, and most preferably 0 to 50 psig, and the temperature is about 250° to about 1000° C., preferably about 350° to about 750° C., and most preferably 450° to 650° C.

The process effluent or product stream generally contains the desired olefins which can be separated by any known methods such as, for example, distillation or fractionation distillation. Because the separation methods are well known to one skilled in the art, the description thereof is omitted herein.

After the catalyst composition has been deactivated by, for example, coke deposition or feed poisons, to an extent that the feed conversion and/or the selectivity to the desired olefins have become unsatisfactory, the catalyst composition can be reactivated by any means known to one skilled in the art such as, for example, calcining in air to burn off deposited coke and other carbonaceous materials, such as oligomers or polymers, preferably at a temperature of about 400° to about 650° C. The optimal time periods of the calcining depend generally on the types and amounts of deactivating deposits on the catalyst composition and on the calcination temperatures. These optimal time periods can easily be determined by those possessing ordinary skills in the art and are omitted herein for the interest of brevity.

The following examples are presented to further illustrate this invention using propane as hydrocarbon feed and are not to be construed as unduly limiting the scope of the present invention. The examples illustrate the preparation of catalyst compositions of the invention and the use of the composition in a hydrocarbon conversion process.

EXAMPLE I

This example illustrates the preparation of several dehydrogenation catalysts.

Catalyst A (comparison) was a platinum/tin-promoted zinc aluminate/calcium aluminate (ZnAl$_2$O$_4$/CaAl$_2$O$_4$) catalyst (prepared by United Catalysts, Inc., Louisville, Ky., under the direction of Phillips Petroleum Company, Bartlesville, Okla.). Catalyst A had been extruded (length: 3/8 inch, diameter: 1/8 inch) and had been calcined in air at 538° C. for 6 hours. This catalyst contained 32.4 weight % Zn, 27.8 weight % Al, 1.17 weight % Ca, 1.29 weight % Sn, 0.65 weight % Pt, and trace amounts of Si and Ti (i.e., less than 0.1 weight % of each). Catalyst A and its preparation are broadly disclosed in U.S. Pat. No. 5,073,662.

Catalyst B (comparison) was silica-bound bismuth oxide (Bi$_2$O$_3$). It was prepared by mixing 4.20 grams of Bi$_2$O$_3$ with 14.50 grams of an aqueous colloidal silica solution (Ludox® AS-400; containing about 40 weight % SiO$_2$; a product of E. I. DuPont De Nemours and Company; marketed by Aldrich Chemical Company, Inc., Milwaukee, Wis.). The mixture was extruded so as to make 1/16 inch extrudates. The extrudates were calcined in air at 538° C. for 6 hours.

Catalyst C (invention) was a physical mixture (blend) of approximately equal volumes of Catalyst A and Catalyst B. The weight ratio of Catalyst A to Catalyst B was about 1.8:1.

EXAMPLE II

This example illustrates the use of the catalysts of Example I in the dehydrogenation of propane in the presence of steam as a diluent.

A stainless steel tube (inner diameter: 1 cm; length: 60 cm) was filled with a mixture of 5 ml Catalyst A and 5 ml Alundum® (inert, low surface area alumina), or with 8 ml Catalyst B, or with 10 ml Catalyst C. The reactor was heated to a reaction temperature of about 550° C. Propane gas was introduced at a rate of about 15 (±0.6) liters/hour (equivalent to a weight hourly space velocity of about 6 g propane per g catalyst per hour). Steam was introduced as a cofeed at a rate of about 23 ml per hours. The reaction pressure was about 0 psig.

The reactor effluent was cooled (by means of an ice trap) to condense water vapor. The gaseous portion of the reactor effluent was passed through a wet test meter for gas volume measurement, and was analyzed by a gas chromatograph at hourly intervals. Pertinent test results are summarized in Table I.

TABLE I

| Catalyst | Reaction Time (Hr.) | Product Composition (Weight %) | | | | % Conversion of Propane | % Selectivity[b] to Propylene |
|---|---|---|---|---|---|---|---|
| | | $C_1$—$C_2$ HC[a] | Propane | Propylene | $C_4$ + HC[a] | | |
| A (Control) | 3 | 0.3 | 84.2 | 14.8 | 0.7 | 15.8 | 93.5 |
| (Pt/Sn/Zn—CaAl$_2$O$_4$) | 5 | 0.4 | 84.5 | 15.0 | 0.1 | 15.5 | 96.9 |
| | 7 | 0.5 | 87.9 | 11.5 | 0.1 | 12.1 | 95.4 |
| B (Control) | 3 | 0 | 100.0 | 0 | 0 | 0 | — |
| (Bi$_2$O$_3$/SiO$_2$) | 5 | 0 | 100.0 | 0 | 0 | 0 | — |
| | 7 | 0 | 100.0 | 0 | 0 | 0 | — |
| C (Invention) | 3 | 0.6 | 80.7 | 18.6 | 0.1 | 19.3 | 96.5 |
| (Blend of A and B) | 5 | 0.5 | 82.2 | 17.2 | 0.1 | 17.8 | 96.3 |
| | 7 | 0.6 | 81.2 | 18.1 | 0.1 | 18.8 | 96.2 |

[a] HC = hydrocarbons
[b] % Selectivity = weight % of propylene in product divided by % propane feed conversion × 100

Test data in Table I show that in the dehydrogenation of propane in the presence of steam, Catalyst C (a blend of Catalyst A and Catalyst B) was more effective (in terms of propane feed conversion and generally also in terms of selectivity to propylene) than Catalyst A, even though Catalyst B was essentially "dead". This result is most surprising. Additional test data (not described herein) indicated that a blend of Catalyst A and Catalyst B was less effective than Catalyst A when hydrogen gas was used as a cofeed instead of steam.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the disclosure and the claims.

That which is claimed is:

1. A composition consisting essentially of an inorganic support and a promoter selected from the group consisting of Group VA metal, Group VA metal oxide, and combinations thereof.

2. A composition according to claim 1 wherein said inorganic support is selected from the group consisting of clays, inorganic oxides, spinels, and combinations of two or more thereof.

3. A composition according to claim 2 wherein said Group VA metal or metal oxide is bismuth or bismuth oxide.

4. A composition according to claim 1 wherein said inorganic support is silica.

5. A composition according to claim 4 wherein said Group VA metal or metal oxide is bismuth or bismuth oxide.

6. A composition comprising a first catalyst which comprises a first inorganic support, at least one Group IVA metal or metal oxide, and at least one Group VIII metal or metal oxide and a second catalyst which comprises a second inorganic support and at least one Group VA metal or metal oxide wherein said first organic oxide or second inorganic oxide is selected from the group consisting of clays, inorganic oxides, spinels, and combinations of two or more thereof.

7. A composition according to claim 6 wherein said Group VIII metal or metal oxide is selected from the group consisting of platinum, platinum oxides, and combinations thereof.

8. A composition according to claim 6 wherein said Group IVA metal or metal oxide is selected from the group consisting of tin, tin oxides, and combinations thereof.

9. A composition according to claim 6 wherein said Group VA metal or metal oxide is selected from the group consisting of bismuth, bismuth oxides, and combinations thereof.

10. A composition according to claim 6 wherein the weight % of said Group IVA metal or metal oxide in said composition is in the range of from about 0.0001 to about 5%.

11. A composition according to claim 6 wherein the weight % of said Group IVA metal or metal oxide in said composition is in the range of from 0.1 to 1.5%.

12. A composition according to claim 6 wherein the weight % of said Group VIII metal or metal oxide in said composition is in the range of from about 0.0001 to about 5%.

13. A composition according to claim 6 wherein the weight % of said Group VIII metal or metal oxide in said composition is in the range of from 0.1 to 1.5%.

14. A composition according to claim 6 wherein the weight percent of said Group VA metal or metal oxide in said composition is in the range of from about 0.1 to about 50%.

15. A composition according to claim 6 wherein the weight percent of said Group VA metal or metal oxide in said composition is in the range of from 1 to 20%.

16. A composition according to claim 6 wherein the weight percent of said Group IV metal or metal oxide is said composition is in the range of from about 0.005 to about 3%; the weight % of said Group VA metal or metal oxide in said composition is in the range of from about 0.5 to about 40%; and the weight % of said Group VIII metal or metal oxide in said composition is in the range of from about 0.005 to about 3%.

17. A composition according to claim 16 wherein the weight % of said Group IVA metal or metal oxide in said composition is in the range of from 0.1 to 1.5%; the weight % of said Group VA metal or metal oxide in said composition is in the range of from 1 to 20%; the weight % of said Group VIII metal or metal oxide in said composition is in the range of from 0.1 to 1.5%; said Group IVA metal or metal oxide is tin or tin oxide; said Group VA metal or metal oxide is bismuth or bismuth oxide; and said Group VIII metal or metal oxide is platinum or platinum oxide.

18. A composition according to claim 17 wherein said composition consists essentially of said first catalyst and said second catalyst; said first inorganic support is a combination of zinc aluminate and calcium aluminate; and said second inorganic support is silica.

19. A composition comprising a first catalyst which comprises at least one Group IVA metal or metal oxide, at least one Group VIII metal or metal oxide, and at least one first inorganic support; and a second catalyst which comprises at least one Group VA metal or metal oxide and a second inorganic support wherein said first or second inorganic support is selected from the group consisting of inorganic oxides, spinels, and combinations of two or more thereof; the weight percent of said Group IV metal or metal oxide in said composition is in the range of from about 0.005 to about 3%; the weight % of said Group VA metal or metal oxide in said composition is in the range of from about 0.5 to about 40%; and the weight % of said Group VIII metal or metal oxide in said composition is in the range of from about 0.005 to about 3%.

20. A composition according to claim 19 wherein said first inorganic support is a spinel and said second inorganic support is silica; and the metal of said spinel is selected from the group consisting of zinc, magnesium, iron, manganese, calcium, zirconium, molybdenum, ruthenium, rhenium, cobalt, germanium, and combinations of two or more thereof.

21. A composition according to claim 20 wherein the weight % of said Group IVA metal or metal oxide in said composition is in the range of from 0.1 to 1.5%; the weight % of said Group VA metal or metal oxide in said composition is in the range of from 1 to 20%; the weight % of said Group VIII metal or metal oxide in said composition is in the range of from 0.1 to 1.5%; said Group IVA metal or metal oxide is tin or tin oxide; said Group VA metal or metal oxide is bismuth or bismuth oxide; and said Group VIII metal or metal oxide is platinum or platinum oxide.

22. A composition according to claim 21 wherein said composition consists essentially of a spinel having incorporated therein tin or tin oxide and platinum or platinum oxide wherein said spinel is selected from the group consisting of zinc aluminate, calcium aluminate, and combinations thereof; and silica having incorporated therein bismuth or bismuth oxide.

23. A composition comprising: (1) a spinel having incorporated therein Group IVA and Group VIII metal or metal oxide and (2) silica having incorporated therein Group VA metal or metal oxide wherein said spinel is selected from zinc aluminate, calcium aluminate, and combinations thereof, the weight % of said Group IVA metal or metal oxide in said composition is in the range of from 0.1 to 1.5%; the weight % of said Group VA metal or metal oxide in said composition is in the range of from 1 to 20%; the weight % of said Group VIII metal or metal oxide in said composition is in the range of from 0.1 to 1.5%; said Group IVA metal or metal oxide is tin or tin oxide; said Group VA metal or metal oxide is bismuth or bismuth oxide; and said Group VIII metal or metal oxide is platinum or platinum oxide.

24. A process comprising: (1) contacting a first inorganic support with at least one Group IVA compound to produce a first composition; (2) heat-treating said first composition under a condition sufficient to convert said Group IVA compound to its corresponding oxide to produce a heat-treated first composition; (3) contacting said heat-treated first composition with a Group VIII compound to produce a second composition; (4) contacting said second composition will heat to produce composition A; (5) contacting a second inorganic support with a Group VA compound under a condition sufficient to incorporate said Group VA compound into said third inorganic support to produce a third composition; (6) heat-treating said second composition to produce composition B; and (7) combining said composition A and said composition B.

25. A process according to claim 24 wherein said first inorganic support is a spinel whose metal is selected from the group consisting of zinc, magnesium, iron, manganese, calcium, zirconium, molybdenum, ruthenium, rhenium, cobalt, germanium, and combinations of two or more thereof and said second inorganic support is silica.

26. A process according to claim 25 wherein said group IVA compound is selected from the group consisting of tri-n-butyltin acetate, n-butyltin trichloride, di-n-butyldiphenyltin, di-n-butyltin diacetate, di-n-butyltin dichloride, di-t-butyltin dichloride, di-n-butyltin dilaurate, dimethyldiphenyltin, diphenyltin dichloride, hexa-n-butylditin, hexamethylditin, hexaphenylditin, methyltin trichloride, phenyltin trichloride, tetra-n-butyltin, tetraethyltin, tetramethyltin, tetraphenyltin, tetra-i-propyltin, tetra-n-propyltin, tin acetate, tin bromide, tin chloride, tin oxalate, tin sulfate, tin sulfide, and combinations of two or more thereof.

27. A process according to claim 25 wherein said Group VA compound is selected from the group consisting of bismuth acetate, bismuth bromide, bismuth chloride, bismuth 2-ethylhexanoate, bismuth fluoride, bismuth iodide, bismuth neodecanoate, bismuth nitrate, bismuth oxide, bismuth sulfide, bismuth titanate, triphenylbismuth, and combinations of two or more thereof.

28. A process according to claim 25 wherein said Group VIII compound is selected from the group consisting of chloroplatinic acid, platinum chloride (platinic chloride), platinum bromide, platinum iodine, tetramine platinum chloride, tetramine platinum nitrate, tetramine platinum hydroxide, tetrachlorodiamine platinum, and combinations of two or more thereof.

29. A process according to claim 25 wherein said Group IVA compound is a tin compound.

30. A process according to claim 25 wherein said Group VA compound is a bismuth compound.

31. A process according to claim 25 wherein said Group VIII compound is a platinum compound.

32. A process according to claim 25 wherein step (3) is carried out contemporaneously with step (1).

33. A process according to claim 25 wherein said Group IVA compound is selected from the group consisting of tri-n-butyltin acetate, n-butyltin trichloride, di-n-butyldiphenyltin, di-n-butyltin diacetate, di-n-butyltin dichloride, di-t-butyltin dichloride, di-n-butyltin dilaurate, dimethyldiphenyltin, diphenyltin dichloride, hexa-n-butylditin, hexamethylditin, hexaphenylditin, methyltin trichloride, phenyltin trichloride, tetra-n-butyltin, tetraethyltin, tetramethyltin, tetraphenyltin, tetra-i-propyltin, tetra-n-propyltin, tin acetate, tin bromide, tin chloride, tin oxalate, tin sulfate, tin sulfide, and combinations of two or more thereof; said Group VA compound is selected from the group consisting of bismuth acetate, bismuth bromide, bismuth chloride, bismuth 2-ethylhexanoate, bismuth fluoride, bismuth iodide, bismuth neodecanoate, bismuth nitrate, bismuth oxide, bismuth sulfide, bismuth titanate, triphenylbismuth, and combinations of two or more thereof; and said Group VIII compound is selected from the group consisting of chloroplatinic acid, platinum chloride (platinic chloride), platinum bromide, platinum iodine, tetramine platinum chloride, tetramine platinum nitrate, tetramine platinum hydroxide, tetrachlorodiamine platinum, and combinations of two or more thereof.

34. A process comprising: (1) contacting a first inorganic support with at least one Group IVA compound and at least one Group VIII compound to produce a first composition; (2) heat-treating said first composition under a condition sufficient to convert said Group IVA compound and said Group VIII compound to their corresponding oxides to produce composition A; (3) contacting a second inorganic support with a Group VA compound under a condition sufficient to incorporate said Group VA compound into said second inorganic support to produce a second composition;

(4) heat-treating said second composition to produce composition B; and (5) combining said composition A and said composition B wherein said first or second inorganic support is selected from the group consisting of clays, aluminas, silicas, spinels, and combinations of two or more thereof.

35. A composition according to claim 34 wherein said first inorganic oxide is a spinel in which the metal of said spinel is selected from the group consisting of zinc, magnesium, iron, manganese, calcium, zirconium, molybdenum, ruthenium, rhenium, cobalt, germanium, and combinations of two or more thereof;

said group IVA compound is selected from the group consisting of tri-n-butyltin acetate, n-butyltin trichloride, di-n-butyldiphenyltin, di-n-butyltin diacetate, di-n-butyltin dichloride, di-t-butyltin dichloride, di-n-butyltin dilaurate, dimethyldiphenyltin, diphenyltin dichloride, hexa-n-butylditin, hexamethylditin, hexaphenylditin, methyltin trichloride, phenyltin trichloride, tetra-n-butyltin, tetraethyltin, tetramethyltin, tetraphenyltin, tetra-i-propyltin, tetra-n-propyltin, tin acetate, tin bromide, tin chloride, tin oxalate, tin sulfate, tin sulfide, and combinations of two or more thereof;

said Group VA compound is selected from the group consisting of bismuth acetate, bismuth bromide, bismuth chloride, bismuth 2-ethylhexanoate, bismuth fluoride, bismuth iodide, bismuth neodecanoate, bismuth nitrate, bismuth oxide, bismuth sulfide, bismuth titanate, triphenylbismuth, and combinations of two or more thereof; and said Group VIII compound is selected from the group consisting of chloroplatinic acid, platinum chloride (platinic chloride), platinum bromide, platinum iodine, tetramine platinum chloride, tetramine platinum nitrate, tetramine platinum hydroxide, tetrachlorodiamine platinum, and combinations of two or more thereof.

36. A process according to claim 35 wherein said first inorganic oxide is a mixture of calcium aluminate and zinc aluminate; said second inorganic oxide is silica; said Group VIII compound is a platinum compound; said Group VA compound is bismuth oxide; and said Group IVA compound is a tin compound.

37. A process comprising combining composition A and composition B wherein composition A is a platinum- and tin-promoted zinc aluminate and calcium aluminate and composition B is bismuth-promoted silica.

38. A process comprising contacting a fluid which comprises at least one saturated hydrocarbon with a catalyst composition under a condition sufficient to effect the conversion of said hydrocarbon to an olefin wherein said catalyst composition comprises (1) a first catalyst comprising at least one first inorganic support, at least one Group IVA metal or metal oxide, and at least one Group VIII metal or metal oxide, and (2) a second catalyst comprising at least one Group VA metal or metal oxide and at least one second inorganic support.

39. A process according to claim 38 wherein said Group IV metal or metal oxide is selected from the group consisting of tin, tin oxides, and combinations thereof.

40. A process according to claim 38 wherein said Group VA metal or metal oxide is selected from the group consisting of bismuth, bismuth oxide, and combinations thereof.

41. A process according to claim 38 wherein said Group VIII metal or metal oxide is selected from the group consisting of platinum, platinum oxides, and combinations thereof.

42. A process according to claim 38 wherein said hydrocarbon comprises an aliphatic hydrocarbon.

43. A process according to claim 38 wherein said hydrocarbon is propane.

44. A process according to claim 38 wherein the weight ratio of said Group IVA metal or metal oxide in said composition is in the range of from 0.1 to 1.5%.

45. A process according to claim 38 wherein the weight % of said Group VIII metal or metal oxide in said composition is in the range of from 0.1 to 1.5%.

46. A composition according to claim 38 wherein the weight percent of said Group VA metal or metal oxide is in the range of from 1 to 20%.

47. A process according to claim 43 wherein said catalyst composition comprises a first catalyst comprising at least one first inorganic support, platinum, and tin and a second catalyst comprising at least one second inorganic support and bismuth.

48. A process according to claim 43 wherein the weight percent of said Group IV metal or metal oxide in said composition is in the range of from about 0.005 to about 3%; the weight % of said Group VA metal or metal oxide in said composition is in the range of from about 0.5 to about 40%; and the weight % of said Group VIII metal or metal oxide in said composition is in the range of from about 0.005 to about 3%.

49. A process according to claim 38 wherein said contacting is carried out in the presence of steam.

50. A process according to claim 48 wherein said contacting is carried out in the presence of steam.

51. A process for converting an aliphatic hydrocarbon to an olefin comprising contacting said aliphatic hydrocarbon with a catalyst composition wherein said contacting is carried out in the presence of steam; said catalyst composition comprises a first catalyst which comprises at least one first inorganic support, platinum, and tin and a second catalyst which comprises a second inorganic support and bismuth; and said first or second inorganic support is selected from the group consisting of clays, inorganic oxides, spinels, and combinations of two or more thereof.

52. A process according to claim 51 wherein said first inorganic support is a spinel which is a combination of zinc aluminate and calcium aluminate and said second inorganic support is silica.

53. A process according to claim 52 wherein said aliphatic hydrocarbon is propane.

* * * * *

UNITED STATES PATENT AND TRADEMARK OFFICE
CERTIFICATE OF CORRECTION

PATENT NO.    : 5,877,369

DATED         : March 2, 1999

INVENTOR(S)   : An-hsiang Wu and Charles A. Drake

It is certified that error appears in the above-identified patent and that said Letters Patent is hereby corrected as shown below:

Column 11, claim 24, line 59, delete "second" and insert ---third---.

Signed and Sealed this

Eighteenth Day of January, 2000

Attest:

Q. TODD DICKINSON

*Attesting Officer*    *Commissioner of Patents and Trademarks*